(12) United States Patent
Nuthi et al.

(10) Patent No.: US 11,456,070 B2
(45) Date of Patent: Sep. 27, 2022

(54) SYSTEM AND METHOD FOR IDENTIFYING HEALTHCARE ASSETS

(71) Applicant: GE Precision Healthcare LLC, Wauwatosa, WI (US)

(72) Inventors: Sridhar Nuthi, Sussex, WI (US); Anurag Voleti, Lincolnshire, IL (US); Sanjoy Saha, Pewaukee, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 281 days.

(21) Appl. No.: 16/778,711

(22) Filed: Jan. 31, 2020

(65) Prior Publication Data

US 2021/0241887 A1 Aug. 5, 2021

(51) Int. Cl.
| | |
|---|---|
| *G16H 40/20* | (2018.01) |
| *G06F 16/22* | (2019.01) |
| *G06F 16/28* | (2019.01) |
| *G16H 40/40* | (2018.01) |
| *G06Q 10/08* | (2012.01) |
| *H04W 4/80* | (2018.01) |
| *G06K 7/10* | (2006.01) |

(52) U.S. Cl.
CPC ......... *G16H 40/20* (2018.01); *G06F 16/2272* (2019.01); *G06F 16/282* (2019.01); *G06Q 10/0875* (2013.01); *G16H 40/40* (2018.01); *G06K 7/10297* (2013.01); *H04W 4/80* (2018.02)

(58) Field of Classification Search
CPC .... G16H 40/20; G16H 40/40; G06F 16/2272; G06F 16/282; G06F 16/2246; G06Q 10/0875; G06K 7/10297; H04W 4/80; H04W 4/70
See application file for complete search history.

(56) References Cited

U.S. PATENT DOCUMENTS

| | | |
|---|---|---|
| 2007/0152047 A1 | 7/2007 | Tu |
| 2016/0364682 A1 | 12/2016 | Jones |
| 2018/0096292 A1 | 4/2018 | Debusk |

FOREIGN PATENT DOCUMENTS

CN 109034955 A * 12/2018

OTHER PUBLICATIONS

International Application No. PCT/US2021/015042 filed Jan. 26, 2021—International Search Report and Written Opinion dated May 11, 2021; 11 pages.

* cited by examiner

*Primary Examiner* — Linh Giang Le
(74) *Attorney, Agent, or Firm* — Andrus Intellectual Property Law, LLP (57) ABSTRACT

A system for identifying healthcare assets includes a set of tags configured to communicate with one another, the set of tags including a root tag configured to transmit an asset identifier identifying the healthcare asset and a plurality of component tags each configured to transmit a component identifier identifying a component of the healthcare asset. A receiver system is configured to receive the asset identifier and the plurality of component identifiers from the set of tags and to automatically generate a bill of materials (BOM) for the healthcare asset based on the asset identifier and the plurality of component identifiers.

20 Claims, 7 Drawing Sheets

SYSTEM AND METHOD FOR IDENTIFYING HEALTHCARE ASSETS

BACKGROUND

The present disclosure generally relates to systems and methods for identifying healthcare assets, and more particularly to systems and methods for automatically generating a bill of materials for a healthcare asset and/or monitoring a healthcare asset throughout its life span.

Healthcare assets, such as computer tomography (CT) imagers, magnetic resonance (MR) imagers, positron emission tomography (PET) imagers, ultrasounds imagers, C-ARM or other x-ray imagers etc., are widely used for diagnoses, treatment, and monitoring of patients. Healthcare facilities, such as hospitals and clinics, are heavily dependent on the apparition, efficiency, and performance of these assets. Failure of these healthcare assets cannot be afforded, and thus many healthcare assets are subjected to monitoring and preventative maintenance which involves periodic maintenance and repair or replacement of key elements of such assets. These assets are complicated systems with many parts that may be repaired or replaced throughout the life of the asset.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a system for identifying healthcare assets includes a set of tags configured to communicate with one another, the set of tags including a root tag configured to transmit an asset identifier identifying the healthcare asset and a plurality of component tags each configured to transmit a component identifier identifying a component of the healthcare asset. A receiver system is configured to receive the asset identifier and the plurality of component identifiers from the set of tags and to automatically generate a bill of materials (BOM) for the healthcare asset based on the asset identifier and the plurality of component identifiers.

One embodiment of the method of identifying a healthcare asset includes providing a set of tags configured to communicate with one another and configuring the set of tags into a hierarchical structure based on a component structure of the healthcare asset. The tags are then operated to communicate an asset identifier identifying the healthcare asset and a plurality of component identifiers identifying components of the healthcare asset. The asset identifier and the plurality of component identifiers are received at a receiver system, which then generates a BOM for the healthcare asset based on the asset identifier and the plurality of component identifiers.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The inventors have recognized a need for modeling each specific healthcare asset in the field, such as large imaging devices (e.g., CT, MR, PET imagers) as well as portable imagers (e.g., ultrasounds imagers, C-ARM or other portable x-ray imagers), as well as other types of high-value and complex healthcare assets. These complex assets have hundreds or even thousands of parts that may be maintained or replaced throughout the life of the asset. The inventors have recognized a need for a system and method that can automatically generate and manage a bill of materials (BOM) for an asset that can track the lineage of an asset and all of its components throughout the life of that asset. The thorough and up-to-date BOM provides a digital model of the asset that can be used for many engineering, service, and commercial purposes. For example, the BOM can be utilized to predict needed maintenance for an asset based on the particular parts, materials, origination, etc. of all components of that asset. Moreover, BOMs across a line of assets can be utilized to monitor trends and trace problem sources, such as tracing a problem back to a manufacturing or other origination point of a group of assets or asset components. Moreover, the BOM can be utilized to monitor asset maintenance over the life of the asset and/or to ensure that authentic parts and proper maintenance are performed according to a predefined schedule.

In view of the foregoing needs in the relevant field recognized by the inventors, the disclosed system and method were developed for identifying healthcare assets that includes a set of tags configured to communicate with one another and a receiver system configured to receive information from the tags in order to automatically generate a BOM for the tagged healthcare asset or any subsystem thereof. In one embodiment, the set of tags may be configured into a hierarchical structure based on a component structure of the healthcare asset. The tags are operated to communicate an asset identifier identifying the medical asset and a plurality of component identifiers identifying components of the medical asset to a receiver system. In one embodiment the hierarchical structure includes a root tag and a plurality of component tags. The root tag is configured to transmit an asset identification identifying the healthcare asset. Each of the plurality of component tags is configured to transmit a component identifier identifying a component, which may be an individual part of a subsystem of the healthcare asset. In one embodiment, the component tags are further hierarchically differentiated into parent and child relationships that follows the component structure of the healthcare asset.

In one implementation, the tags are configured to communicate as a mesh network, and thus to route data non-hierarchically, though their identities may still be defined hierarchically based on the components structure of the healthcare asset. In other embodiments, the tags may be configured to communicate hierarchically such as to originate messaging at the lowest node level and propagate messages upward through the hierarchical structure. In such an embodiment, the root tag and/or some subset of tags at the top of the hierarchy may be configured to communicate with the receiver system. As will be recognized by a person having ordinary skill in the art in view of the present disclosure, various communication protocols and wireless or wired communication means may be implemented in order to execute the disclosed system and methods including for communication among the set of tags on a healthcare asset and for communication between the set of tags and the receiver system.

Figure 1:
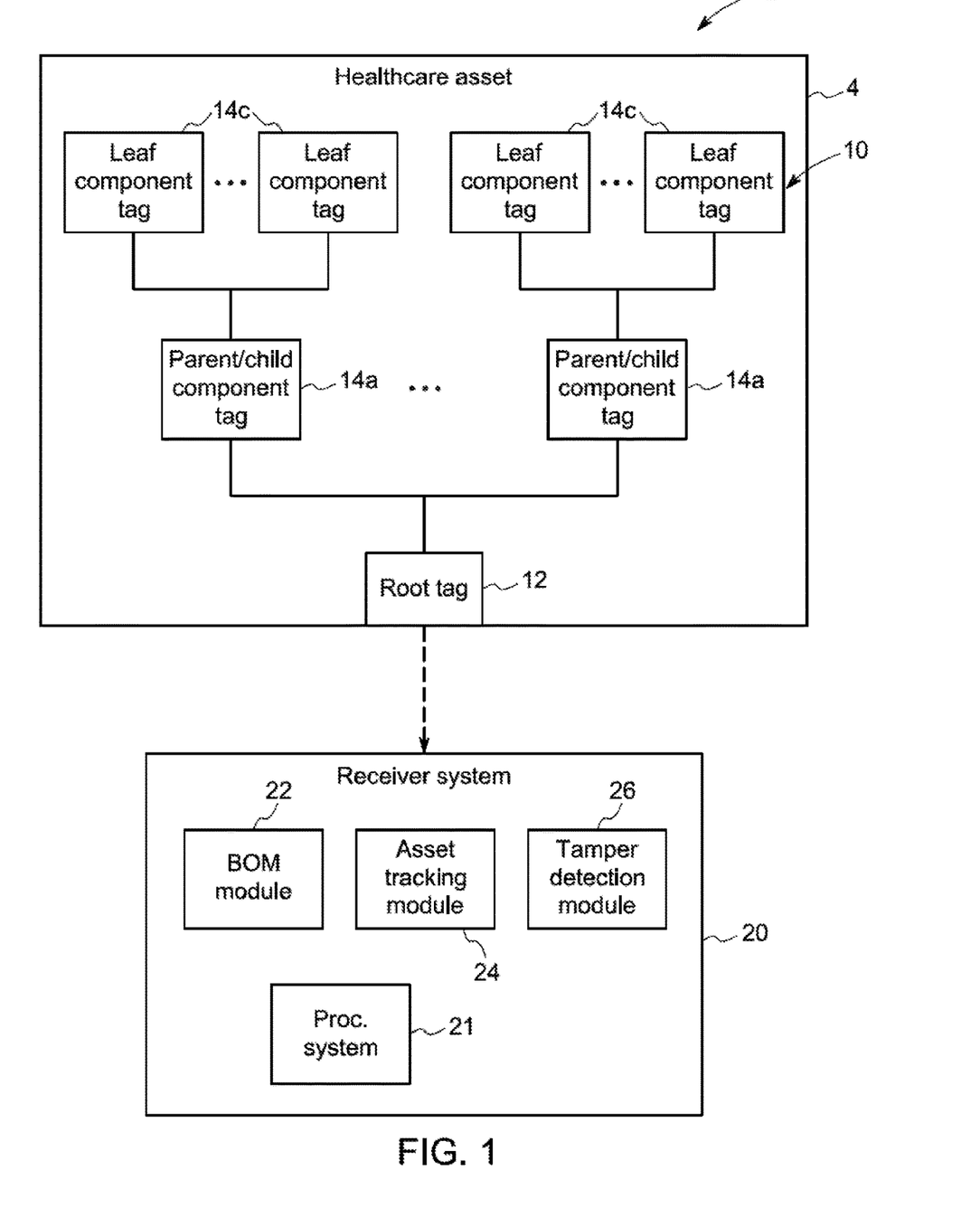
FIG. 1 schematically represents an exemplary system for identifying healthcare assets.

FIG. 1 schematically depicts one embodiment of a system 2 for identifying a healthcare asset 4. A set of tags 10 includes a root tag 12 and a plurality of component tags 14. The component tags 14 are each configured to be associated with and identify a component of the healthcare asset 4. For example, each component tag 14 may store a component identifier that identifies a component of the healthcare asset 4. In one embodiment, the plurality of component tags may be hierarchically structured into parent/child relationships including one or more levels of parent/child tags 14a, 14b (see also FIG. 2) and leaf tags 14c. Each parent/child tag has a parent tag above it in the hierarchical structure, which may be another parent/child tag 14a, 14b or may be the root tag 12. Each parent/child tag also has one or more child tags beneath it in the hierarchical structure, which may be another parent/child tag 14a, 14b or may be a leaf tag 14c. One or more leaf tags 14c are at the ends of the hierarchical structure, where each leaf tag 14c has a parent tag but no child tag.

The set of tags 10 is configured to communicate with a receiver system 20, and in particular to communicate the asset identifier for the healthcare asset 4 and the plurality of the component identifiers identifying the components thereof. The receiver system 20 includes software, such as the BOM module 22, the asset tracking module 24, and/or the tamper detection module 26 configured to perform various asset identification and tracking functionality based on the information received from the set of tags 10. The receiver system 20 includes a processing system 21 that executes the software 22, 24, 26 stored within the receiver system 20. In various embodiments, the receiver system 20 may be any computing system, which may be anything from a server to a mobile device, or a network of computing systems. For example, the receiver system 20 may be implemented on a cloud computing system.

Figure 2:
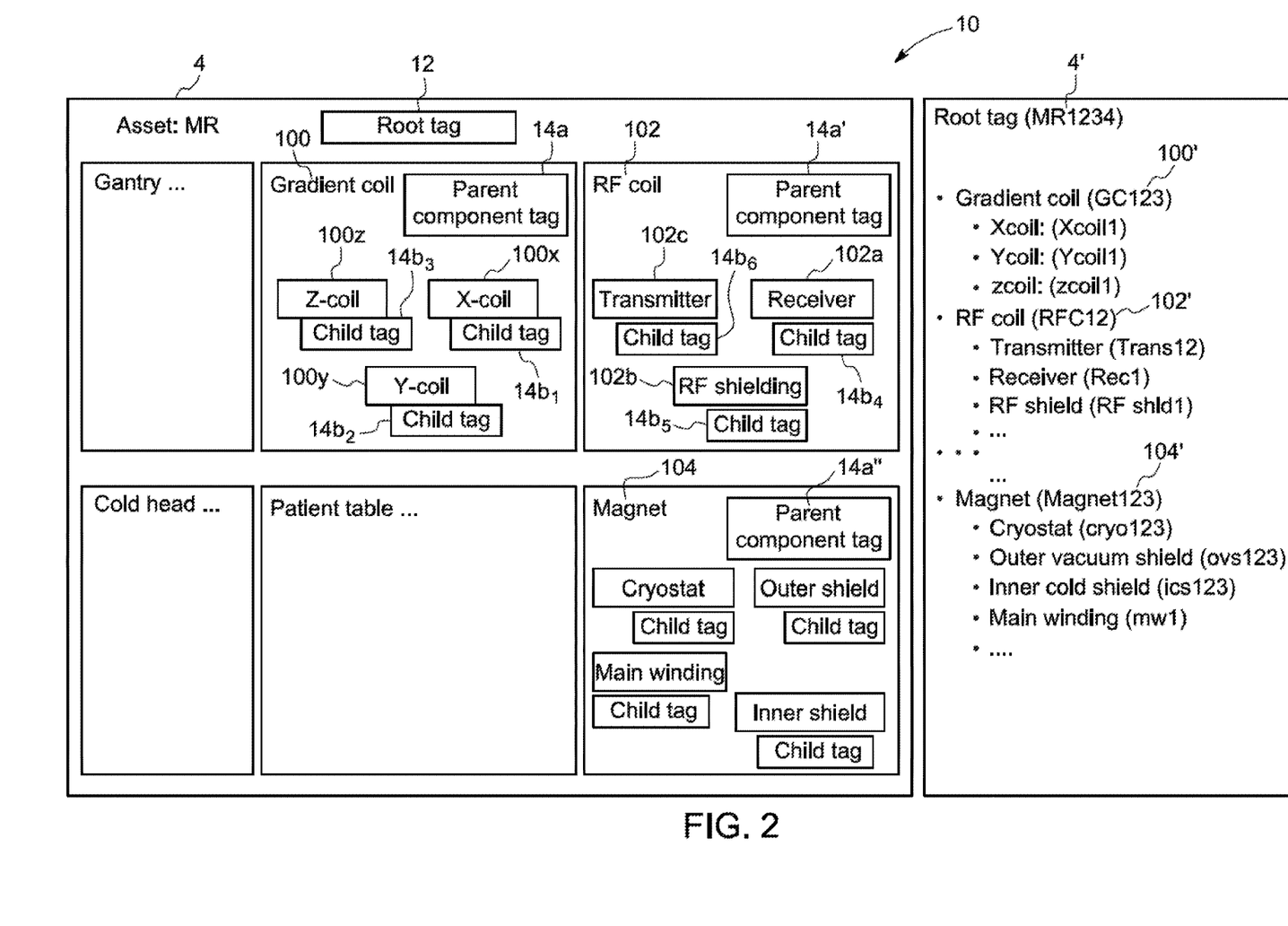
FIG. 2 demonstrates a set of tags in a system for identifying healthcare assets in accordance with one embodiment of the present disclosure.

The healthcare asset 4 identified by the set of tags 10 may be any type of healthcare asset having multiple component parts for which BOM generation and tracking is valuable. FIG. 2 represents one embodiment of a healthcare asset 4, which is an MR imager. A root tag 12 is configured to identify the MR asset 4, and stores an asset identification number that identifies the MR asset. A plurality of component tags 14 are each associated with a component of the MR asset 4. MR imagers are complex systems and thus the set of tags 10 may include several hundred, or even several thousand, tags labeling the various components of the MR system. Multiple component tags may be associated with each of multiple subsystems within the MR asset 4, such as the gradient coil, the RF coil, the magnet, the gantry, the cold head, the patient table, etc. FIG. 2 provides a few examples for purposes of explanation into illustrate the component tag structure; however, a person of ordinary skill in the art will understand in view of this disclosure that any of a large number of components in a given MR system may be tagged.

For the gradient coil 100, a parent component tag 14a is configured to transmit an identifier 100' for the gradient coil that identifies the particular gradient coil incorporated in the MR asset 4 for purposes of the BOM. Similarly, a parent component tag 14a' is associated with the RF coil 102 by being configured to and storing the asset identification 102' for that RF coil. Similarly, a parent component tag 14a" is associated with the magnet by storing and being configured to transmit the component identifier 104' for the particular magnet 104 incorporated in the particular MR asset 4. In various embodiments, the component identifiers stored on each tag 14a, 14b, 14c are configured to identify the type of component (e.g., gradient coil, X/Y/Z coil, RF coil, transmitter/receiver/RF shield, etc.) as well as the exact instance of that component (e.g., by a serial number or some other unique identifier). In some embodiments, the component identifiers identifying particular hardware components may be traceable to specify particular manufacturing origins, product and/or material lots, software versions, assembly lines, etc. to identify the origin of the component.

In the hierarchical structure, the parent tags 14a, 14a', 14a" identify the root tag 12 as their parent. Each parent tag 14a, 14a', 14a" has multiple child tags 14b that represent components within the respective subsystems 100, 102, 104 represented by those parent component tags. In the depicted example, the parent component tag 14a configured to identify the gradient coil 100 has three child tags 14b1, 14b2, 14b3. The child tag 14b1 identifies the X coil 100x, the child tag 14b2 identifies the Y coil 100y, and the Z coil 100z is identified by child tag 14b3. Similarly, the subcomponents of the RF coil 102 are each associated with a child tag that reports to the parent component tag 14a for the RF coil 102. For example, the receiver 102a is identified by the child tag 14b4, the RF shield 102b is identified by child tag 14b5, the transmitter 102c is identified by child tag 14b6, etc. Likewise, the magnet 104 identified by parent tag 14a", has multiple child tags associated therewith representing each of the outer shield, inner shield, main winding, cryostat, etc. Each child tag 14b2 stores and is configured to transmit a component identifier that identifies the respective component 100x, 100y, 100z, 102a, 102b, 102c, etc., including the component type and the specific component instance (e.g., serial number or other unique identifier). This information then gets transmitted from the set of tags 10 to the receiver system 20, as is described herein for various embodiments.

Each component tag 14 is configured to store, in addition to the component identifier, information relating to its position within the hierarchical structure. In one embodiment, configuring the plurality of component tags 14 includes storing a parent ID on each component tag that identifies the parent therefor. Thus, each parent component tag 14a in the example at FIG. 2 stores the parent ID for the root tag 12, which in the depicted example is the MR asset identifier 4'. Each child tag 14b stores a parent ID for the parent component tag 14a for the subsystem for which it belongs. Thus, child tags 14b1, 14b2, and 14b3 each store the parent ID for the parent component tag 14a, which in one example may be the gradient coil identifier 100'. As will be understood by a person having ordinary skill in the art in view of this disclosure, each child tag described in this example may be a parent to another child tag, and such further child tags would similarly store the parent ID of the child tags shown in FIG. 2 (e.g. 14b1, 14b2, 14b3). And further levels of hierarchy are provided down to the smallest subcomponent being tracked, which is identified by a leaf tag 14c.

Where each tag is originally configured with a component identifier and a parent ID, the set of tags 10 may be configured to automatically map the hierarchical structure based on communication between parent and child tags. Each parent component tag 14a may be configured to identify and store its child component tags as those tags transmitting a corresponding parent ID that identifies that parent tag. Thus, each tag 12, 14 is also configured to store and identify itself—i.e., to store its own identifier. Thus, each component tag 14 is configured to recognize transmission of its own identifier by a child tag, and thereafter to track and listen to messages from the child tags 14b transmitting that identifier as the parent ID.

Figure 3:
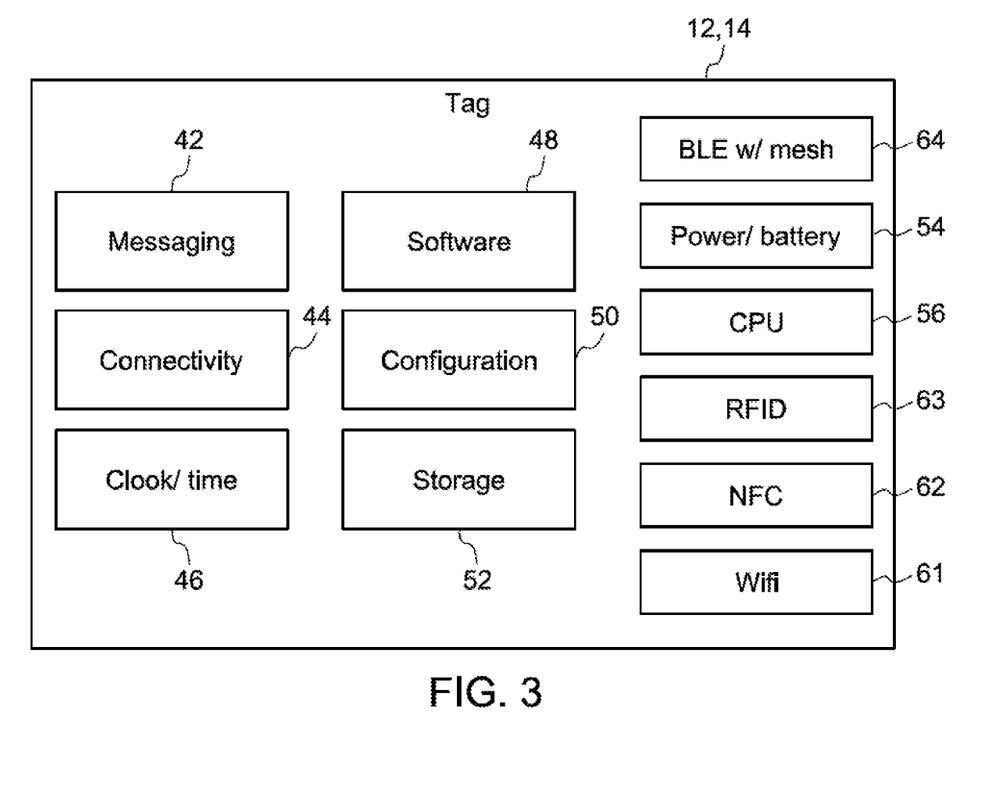
FIG. 3 schematically represents an exemplary tag in accordance with one embodiment of the present disclosure.

Each tag 12, 14 may be configured as either an external tag that is a unit that gets attached, such as physically adhered to, each component of the asset 4, or may be an integrated tag that is manufactured as part of and/or otherwise integrated into the asset. FIG. 3 represents one embodiment of a tag 12, 14. Various tag configurations may include a subset of the elements depicted in FIG. 3, such as depending on the hierarchical position of the tag and/or the system configuration. Each tag 12, 14 includes one or more functional modules 42-52, which may cooperate in conjunction with the CPU 56 and/or the wireless communication modules 61-64 in order to function as described herein. In various embodiments, one or more of the tags 12, 14 may be a passive tag that is externally powered or it may be an active tag containing an internal power source. Each tag 12, 14 may have a power module 54 which may be cell powered or may include a battery as a DC power source. The power module 54 may further include power control functionality such that the tag 12, 14 can enter various power states, such as a no power or low power passive mode which may be engaged when the tag 12, 14 is not transmitting and/or in a low battery or unpowered condition.

Each tag 12, 14 may have a messaging module 42 that facilitates communication with other tags and/or with the receiver system 20. The messaging module 42 may be configured to support events, i.e. event generation upon detection of an abnormality with the tag 12, 14 or with a child or parent tag related thereto, notifications, pay load, etc. The messaging module 42 may be configured to manage multicast and/or broadcast messaging, depending on the system 2 configuration.

Each tag 12, 14 may have a connectivity module 44 configured to manage the communication connectivity between the particular tag 12, 14 and its family members, and/or with the receiver system 20. In various embodiments, the tag 12, 14 may include various different wireless communication receiver/transmitters configured for communicating via various different wired or wireless protocols, including a Wi-Fi module 61 configured to communicate on a Wi-Fi network, a near field communication (NFC) chip 62 configured to enable NFC communication, such as with a portable receiver system, a Bluetooth low energy (BLE) module 64, such as a Bluetooth transceiver configured for mesh networking to enable many-to-many communication over Bluetooth radio.

Certain tags 12, 14 may further include a radio-frequency identification (RFID) chip 63 that enables RFID communication, such as for purposes of location tracking. For example, a root tag 12 or high level component tag 14 on a portable healthcare device, such as a portable ultrasound, may include an RFID chip 63 that enables location tracking of the asset 4, such as via a real-time locating system (RTLS) or other RFID-based tracking systems. Alternatively, other types of tracking systems, such as Wi-Fi-based tracking, may be utilized instead of RFID. For stationary assets 4 where asset tracking is unnecessary, such as MR and CT scanners, the RFID chip 63 and asset tracking functionality may be eliminated.

Each tag 12, 14 may have a clock module 46 configured to keep track of time for the purpose of synchronizing messaging, time-stamping events, and tracking time for purposes of periodic messaging (e.g., "heart-beat" status messaging for purposes of asset monitoring, as described below). Each tag 12, 14 may include various software instruction sets that provide logic for handling various connectivity and messaging needs, including for communication between tags within the set 10 and/or communication with the receiver system 20, for tags enabled for such communication. Software 48 may also be provided for detecting and managing events and related notifications, etc.

Each tag may include one or more configuration files 50 that contains the setup profile for the tag 12, 14. The configuration file 50 includes, for example, the component identifier or asset identifier for the relevant tag, a hierarchy category or position (e.g., root, parent, child, leaf), a subsystem classification, (e.g., scanner, generator, tube, gantry, gradient coil, etc.), or component description (Z coil, RF shield, etc.), family descriptor (where the component tag belongs on the hierarchical structure), the parent ID (for all but the root tag) that relates a particular tag 14 to its parent in the hierarchical structure, and the like.

Each tag 12, 14 may include a storage system 52 providing temporary storage of a payload before transmission, as well as available storage for accommodating various on-demand storage needs, such as for failure of the wireless transmitter and/or the wireless communication system, low battery scenarios, etc. Namely, the storage 52 may be configured to store information generated by the various other modules 42-50 when such information has not yet been transmitted or cannot be transmitted for some reason.

Each tag is configured for its particular role in the hierarchy, and thus different hardware and software configurations may be provided for the various tags 12, 14a, 14b, 14c in the system 2. Where the tags are external tags configured for attachment to a component of the asset 4, different tag types may be provided with hardware configurations geared toward a particular tag role—i.e., root, parent/child, leaf, etc. For example, a root tag 12 may include more data communication modules 61-64 to support multiple communication options for various communication needs, such as communication between tags, communication with one or more receiver systems 20, communication with a location tracking system (e.g., RFID), etc. In certain embodiments, the system 2 may include multiple receiver systems 20, such as a server system and a portable receiver system, and thus the root tag 12 may be configured to communicate with each receiver system 20 by various protocols, such as TCP/IP, UDP, NFC, NDEF, GATT, etc.

Similarly, each tag type may have certain software functionality configured for performing the functions of that tag in the hierarchy. In certain embodiments, the system 2 may be sold or offered as a set of tags 10 and receiver system, where the set of tags 10 include a root tag 12 preconfigured for performing the necessary functionality and one or more different types of component tags, such as parent/child tags, system-level parent tags configured for high level functionality in the hierarchy, leaf tags, etc. In certain embodiments, each tag type may contain a visual identifier that visually differentiates the tag type within the set 10. For example, the root tag may have a root tag visual identifier that distinguishes it as the root tag 12. The plurality of component tags may have component tag visual identifiers, which may be different visual identifiers to identify the type of component tag (e.g., system-level parent, mid-level parent/child, leaf, etc.). For example, the visual identifiers may be a color, text, and/or numerical label identifying the tag type.

Figure 4:
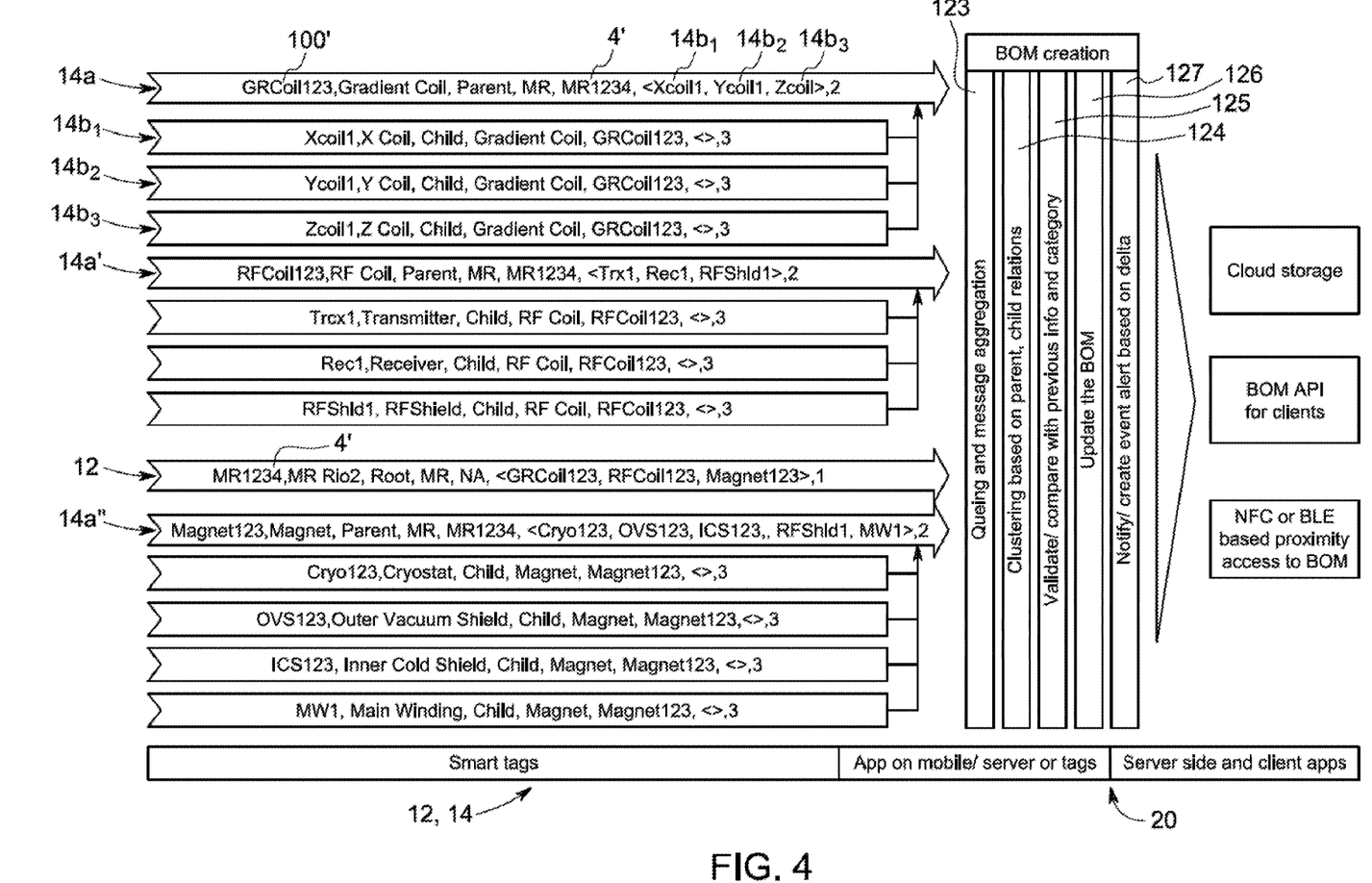
FIG. 4 is a flow chart depicting one embodiment of bill of material (BOM) generation in accordance with an exemplary embodiment.

FIG. 4 is a flow chart exemplifying tag communication for the MR asset shown in FIG. 2 and BOM creation functionality. In the depicted example, each tag 12, 14 transmits its component identifier (or asset identifier in the case of the root tag) along with the component identifiers of its children, and its parent ID. Thus, the set of tags 10 in the depicted embodiment has already been configured such that each tag knows its parent, which in one embodiment is established as an initial configuration step and its children (which may be established as a subsequent configuration step). Additionally, each tag may transmit other configuration information, such as its category (root, parent, child) its system or component description ("MR Rio2," "gradient coil," etc.) a hierarchical level identifier (level 1, level 2, level 3), or the like.

In the depicted example, each system-level parent component tag 14a, 14a', 14a" transmits the information of its parent ID for identifying the root tag and the information of its children 14b. The parent component tag 14a for the gradient coil 100, for example, transmits the component identifier 100' identifying the gradient coil, a system description of the gradient coil, its tag category (or tag type) its parent ID 4', a description of the asset 4 to which it belongs, and the component identifiers 14b₁-14b₃ of its children, as well as its hierarchical level (level 2). The system-level parent component tags 14a' and 14a" transmit similarly-structured messages for their system components. Each child 14b₁-14b₃ first transmits its component identifier, component description, etc., which is received at the system-level parent component tag 14a, which then relays the child-transmitted information in its own transmission.

The root tag 12 listens for transmissions from its children, which are the system-level parent component tags 14a, and includes some or all of the information transmitted from the parent tags 14a in the root tag transmission. In the depicted example, the system-level parent component tags 14a and the root tag 12 are configured to transmit information to the receiver system 20. The child tags 14b (and any leaf tags 14c) do not transmit via the communication protocol established for the receiver system 20, and thus only communicate on the tag network, such as the multicast or broadcast network established for inter-tag communication. In other embodiments, only the root tag 12 may be configured for communication with the receiver system 20, and thus the system-level parent tags 14a may only communicate within the tag network, and all messages and information from all tags in the set 10 are communicated through transmissions from the root tag 12. In other embodiments, child tags 14b may be configured for communicating with the receiver system 20 such that the receiver system 20 receives transmission from multiple levels in the tag hierarchy.

The receiver system 20 receives transmission from the tags, which includes the asset identifier and all component identifiers currently operating in the system 2. The receiver system 20 is configured to generate one or more BOMs based on the information transmitted by the tags. In one embodiment, the receiver system 20 includes a BOM module 22, which is a set of software instructions configured to compile the transmitted information into an up-to-date BOM for the healthcare asset 4 or any subsystem BOM for any subsystem within the asset 4 (e.g., subsystems 100, 102, 104 of the MR asset). FIG. 4 depicts exemplary steps for BOM creation which, for example, may be performed by the BOM module 22. First, the transmitter information may be queued and aggregated. In one embodiment, the transmitted messages are queued based on transmission time. In certain embodiments, the system may be configured with priority messaging capabilities where certain key components, such as components relating to patient safety and/or components that are fundamental to safe operation of the healthcare asset 4, may transmit messages with a priority code. The queueing and messaging aggregation step 123 will prioritize those messages accordingly, such as ahead of earlier-occurring messages.

The aggregated messages are then clustered at step 124, such as based on their parent/child relations. This organizes the messages in a coherent way based on the asset for configuration, and functions to cluster messages that are likely to contain redundant information together. The various messages are then validated, such as by comparing the messages from various devices to one another and/or comparing the messages to previous transmissions from the same tags. An updated BOM is then generated at step 126 based on the transmitted messages. At step 127, the BOM module 22 reviews the updated BOM to determine whether any event alerts should be generated that identify missing components or other problems with the asset 4.

Where one or more tags is missing, such as due to component removal, where the component containing the tag is removed from the asset 4 system, or tag failure, a missing component event may be created at the tag-level and communicated to the receiver system 20. For example, a parent tag may be configured to detect when it does not receive a component identifier from one of its child component tags—i.e., a non-transmitting tag—and then generate a missing component event. The missing component event may propagate up through the hierarchical structure of the set of tags 10 and be transmitted to the receiver system 20. Alternatively, each parent tag may be configured to only transmit information received from its children, and any missing component will be detected at the receiver system 20 level by the BOM module 22, which may be configured to detect the missing component tag by identifying any missing component identifiers from a transmission. In such an embodiment, the BOM module 22 may compare the updated BOM to a previously-generated BOM for the healthcare asset 4 in order to identify any missing component identifiers, and to generate a missing component alert accordingly. For example, such alerts may be provided to a user, such as through a user interface for the receiver system 20.

Various systems and methods may be provided for user access to information aggregated and generated by the receiver system 20. Additionally, multiple receiver systems 20 may be incorporated within the asset identification system 2. In one embodiment, a primary receiver system 20 may be incorporated within a host network associated with a healthcare facility such as a hospital or other environment wherein the healthcare asset 4 is utilized. The receiver system 20 may be housed within a server on the host network, which may be an on-site network or a cloud system. Alternatively or additionally, a portable receiver system may include a portable reader configured to wirelessly communicate with one or more of the tags 12, 14, such as by relatively short-range wireless communication means. For example, one or more of the tags in the set 10, such as the root tag 12 and/or system-level parent tags 14a, may be configured for NFC communication with a portable reader held in close proximity thereto in order to extract information therefrom. Alternatively or additionally, the tag 14 may be configured for BLE communication for the same purpose. Thereby, the system 2 enables on-demand and on-location information gathering for a particular healthcare asset 4.

Figure 5:
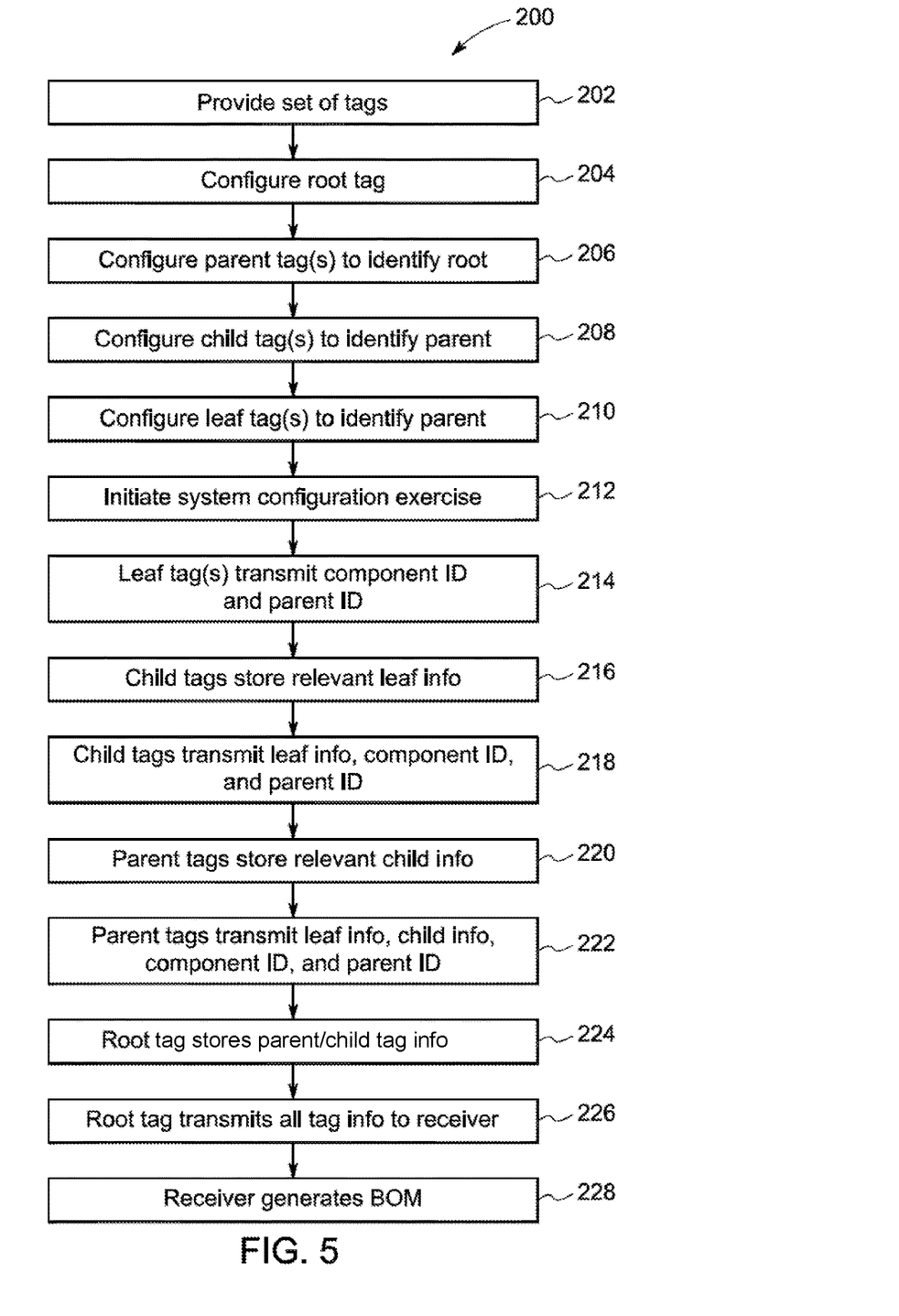
FIGS. 5-8 depict exemplary methods for identifying a healthcare asset in accordance with embodiments of the present disclosure.

FIGS. 5-8 depict exemplary embodiments of methods 200 for identifying healthcare assets, including methods of configuring and operating various embodiments of the system 2. FIG. 5 depicts one embodiment of system configuration steps for configuring a set of tags 10 into a hierarchical structure based on component structure of a healthcare asset. A set of tags are provided at step 202. A root tag is configured at step 204, such as by storing an asset identifier for the healthcare asset. Additional configuration information may be stored in the configuration file 50, as described above, such as information identifying a description of the asset the tag type, etc. Additionally, software 48 may be configured for enabling the root tag 12 functionality, as well as messaging and connectivity configurations needed for communicating with the receiver system 20 and communicating on the tag network.

A plurality of component tags 14 are then configured according to the hierarchical structure representing components of the healthcare asset 4. One or more parent tags are configured at step 206, including by storing the relevant component ID and to store the parent ID. For the system-level parent component tags 14a representing the first level beneath the root tag 12, the parent ID will identify the root tag 12. Each subsequent tag level is then configured, where each of the child tags are configured to identify their parent at step 208. The one or more leaf tags 14c are lastly configured at step 210, including storing their relevant component identifiers and parent ID that identify the child tag 14b immediately above the leaf tag.

A system configuration exercise is then initiated at step 212. For example, system configuration may be initiated by the root tag 12 for the receiver system 20. In one embodiment, the configuration exercise starts at the leaf tag level, where each leaf tag transmits its component identifier and its parent ID at step 214. Each child tag then stores the information for any leaf tag associated therewith at step 216. Namely, each child tag 14b identifies messages containing its identifier in the parent ID position, and the child tag then identifies each such leaf tag as its child and stores the information transmitted therefrom. The child tag then performs its own transmission at step 218, where it transmits its component identifier and its parent ID, along with the leaf information transmitted from its child/leaf tags.

This process is repeated up the hierarchical tag structure, where each parent tag receives and identifies its relevant child tags at step 220, stores the information transmitted from the child and then includes its child information in its own transmission up the tree structure at step 222. Thus, the parent tag transmits the leaf information and all information from the child tags, in addition to its own component identifier and parent ID, such that the transmitted information gets aggregated as it travels up the hierarchical structure. At each level, the parent tag is able to identify its children tags based on their transmission of a corresponding parent ID.

Figure 6:
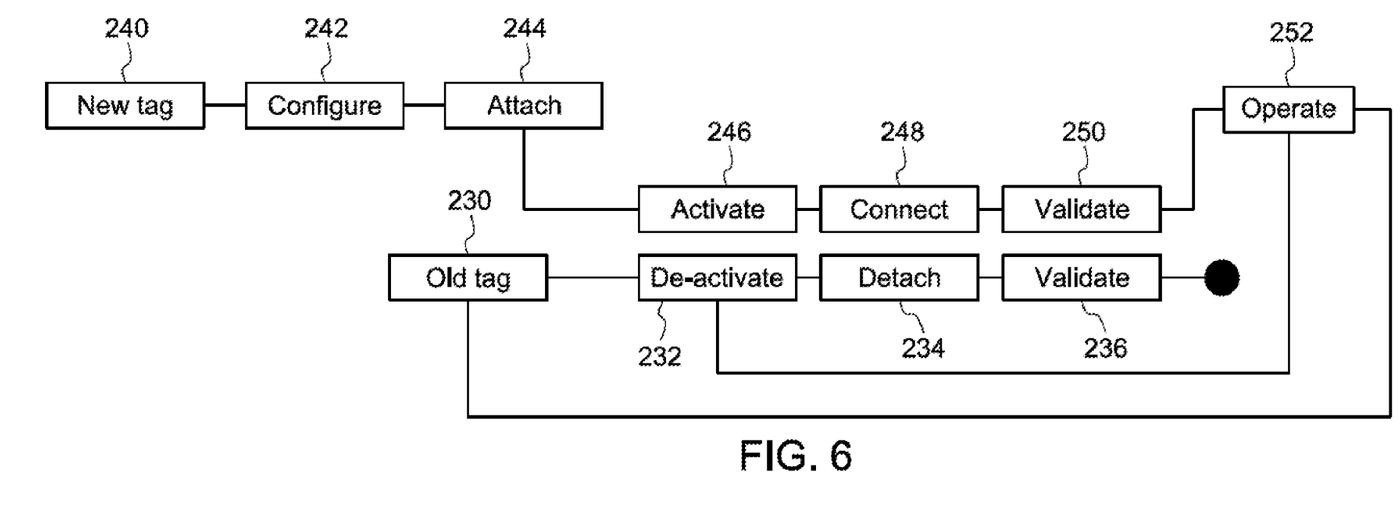
Figure 7:
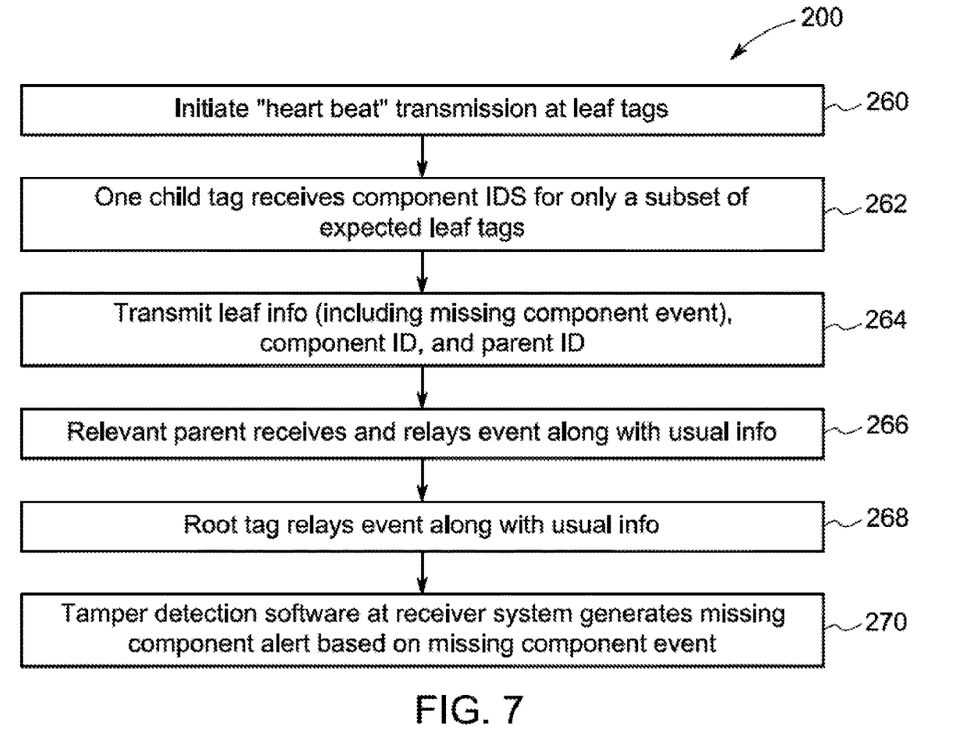

At the top, the root tag identifies its children, such as the system-level parent tags 14a, and stores the information transmitted therefrom at step 224. The root tag then transmits all tag information to the receiver at step 226. Upon receipt of transmission from all the tags, the receiver system 20 generates the BOM at step 228, such as by the steps described above in FIG. 4.

Where the set of tags 10 includes external tag elements adhered or otherwise attached to the asset 4 components, such external tags 12, 14 elements may need to be removed and replaced. For example, an individual tag may be detached, such as after tag failure, and replaced by a new tag. Alternatively, a component of the asset 4 may be replaced and may contain or have attached a new tag that needs to be integrated into the BOM. FIG. 6 depicts method steps for removing an old tag and replacing it with a new tag such that the new tag is integrated into and replaces the hierarchical position in the structured set of tags 10 occupied by the old tag. The old tag is identified at step 230, such as by a technician, and deactivated at step 232. The deactivated tag is detached from the component at step 234 (in the instance where a tag is being removed and replaced), or the entire component to which the tag is attached is removed from the asset 4. A communication sequence is then executed at step 236 to validate the tag removal, such that the set of tags 10 and the receiver system 20 recognize the missing tag. Thereafter, the tag has been successfully removed and the system recognizes the missing tag.

A new tag is then attached at step 240 and configured at step 242, such as to store its component ID and/or parent ID, as described above. The new tag may be an external tag attached to the component or an integrated tag where the tag elements are integrated into the components system. Where only the tag is replaced, the new tag is then attached to the component step 244. Alternatively, where a new component is provided, the new component may contain a new tag which needs to be configured in the system when the new component is installed into the asset 4. The tag is activated at step 246, such as by powering the tag, and connected to the network at step 248. The validation procedure is then repeated at step 250 to generate a new BOM showing the new tag in the appropriate hierarchical location. Once the new tag has been validated, the set of tags 10 and the asset 4 can be operated at step 252 as normal.

In certain embodiments, an asset tracking module may be configured to periodically receive a "heartbeat" transmission from the set of tags 10. For example, communication from the hierarchically configured set of tags 10, such as that represented in FIG. 4, may be generated periodically, such as at a preconfigured period appropriate for the particular asset 4. To provide one example, the periodic transmission, or "heartbeat" period, may be generated daily or weekly. In other examples, the heartbeat transmission may be more frequent such as every hour or several times per day. Other periods for transmission may be provided and are within the scope of the disclosure.

The asset tracking module 24 may be configurable to set the period for the heartbeat transmission and to receive and assess the periodically transmitted information from the set of tags 10. In one such embodiment, a heartbeat transmission process is initiated at step 260, which may be initiated at the lowest level of the hierarchical structure and propagated upwards. Thus, the leaf tags 14c may each transmit their respective component identifier and parent ID, and the messaging may propagate up the hierarchical structured set of tags 10, as described above. Where one tag in the system does not receive transmission from a child tag as expected, an event may be generated. In the example at FIG. 7, one child tag receives component IDs for only a subset of the expected leaf tags. Thus, one or more leaf tags are not transmitting, either because the tag(s) are not operating or the component to which the tag(s) is attached has been removed. Of particular concern, scenarios occur where a component of a healthcare asset 4 is removed and replaced with an unapproved component, such as an aftermarket part that is not approved by the manufacturer of the healthcare asset 4. This can be problematic because untested and unapproved substitute components may be of lesser quality or may not function optimally within the healthcare asset 4. The asset tracking module 24 and/or the tamper detection module 26 may be configured to identify this scenario based on transmissions (or missing transmissions) from the set of tags 10. Likewise, where one or more tags fails and thus does not transmit as expected, the asset tracking module 24 can be configured to alert a system operator to the tag failure.

Returning to FIG. 7, the child tag that detected the missing leaf tag transmits a missing component event at step 264. For example, the child tag may transmit the information received from the subset of leaf tags along with a missing component event designating the one or more leaf tags that are not active. The child tag also transmits its component ID and parent ID such that the message propagates up system, along with its usual transmitted information represented at step 266. The message propagates up to the root tag 12, which relays the missing component event along with its usual transmission information at step 268. The receiver system 20, and particularly the asset tracking module 24 and/or tamper detection module 26 receive and process the information in order to generate a missing component alert at step 270 specifying the missing component and any situational awareness that can be derived from the missing tag information. For example, if several tags identifying sub components of a larger component system, such information may be provided in the event alert such that the monitoring individual can be aware of any potential problems with the asset 4.

Figure 8:
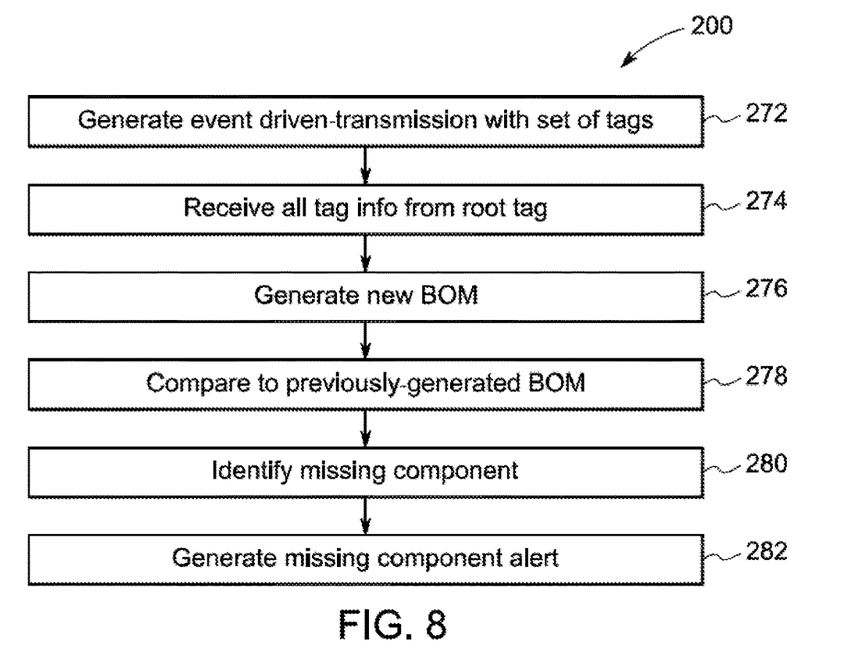

FIG. 8 depicts another embodiment of steps for providing tamper detection, such as may be executed by the set of tags 10 in conjunction with the tamper detection module 26 of the receiver system 20. An event-driven transmission is generated at step 272. For example, a tag may generate a transmission when it is removed from the system, such as where a component is detached from the system, a tag is disconnected, or otherwise. For example, a parent tag may detect a warning transmission from a child tag that may be generated just before the child tag goes offline. The event driven transmission propagates up the hierarchically structured set of tags 10 and all tag information is received at the receiver system 20 from the root tag 12 at step 274. A new BOM is generated at step 276, as described above. The new BOM is compared to one or more previously-generated BOMs at step 278. In one embodiment, the tamper detection module 26 may be configured to identify a missing component or changed component based on the comparison at step 280. Alternatively or additionally, where events are transmitted from the tags, the tamper detection module 26 may identify missing components based thereon. A missing component alert is generated at step 282.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A system for identifying healthcare assets, the system comprising:
   a set of tags each attached to, integrated into, or near the healthcare asset and configured to communicate with one another in a hierarchical structure, the set of tags including:
   a root tag configured to transmit an asset identifier identifying the healthcare asset;
   a plurality of component tags each configured to transmit a component identifier identifying a component of the healthcare asset and based on the hierarchical structure of the set of tags;
   a receiver system configured to receive the asset identifier and the plurality of component identifiers from the set of tags and to automatically generate a bill of materials (BOM) representative of a component structure of the healthcare asset based on the asset identifier and the plurality of component identifiers; and
   wherein the component structure of the healthcare asset is determined based on the hierarchical structure of communications between the tags.

2. The system of claim 1, wherein the plurality of component tags are configured in the hierarchical structure such that each component tag stores a parent ID identifying a parent component tag therefor, wherein each component tag is further configured to transmit its parent ID in conjunction with its component identifier; and
   wherein the receiver system is configured to determine a parent relation for each of the plurality of component tags based on the received plurality of parent IDs, and to generate the BOM representative of the component structure of the healthcare asset based on the parent relations and the hierarchical structure of the set of tags.

3. The system of claim 2, wherein each parent component tag is configured to identify the one or more component tags that transmit the parent ID corresponding thereto as a child component tag.

4. The system of claim 3, wherein each parent component tag is configured to transmit the component identifier from each of its child component tags in conjunction with its component identifier and its parent ID.

5. The system of claim 4, wherein each parent component tag is configured to detect a missing component identifier for a non-transmitting one of its child component tags and to transmit a missing component event.

6. The system of claim 4, wherein the root tag is configured to transmit component identifier from all component tags transmitting in the hierarchical structure.

7. The system of claim 6, wherein root tag is further configured to detect a missing component identifier for a non-transmitting one of its child component tags and to transmit a missing component event, and where in the receiver system is configured to generate a missing component alert identifying the missing component based on the missing component event.

8. The system of claim 6, wherein the root tag is configured to transmit the component identifier from all transmitting component tags in the set of tags.

9. The system of claim 1, wherein the receiver system is further configured to:

compare the plurality of component identifiers from the set of tags to a previously-generated BOM for the healthcare asset; and identify a missing component tag based on the comparison and to generate a missing component alert identifying the missing component.

10. The system of claim 1, wherein the receiver system is further configured to generate a subsystem BOM for one or more subsystems within the healthcare asset.

11. The system of claim 1, further comprising a portable reader configured to wirelessly communicate with the root tag, wherein the root tag is configured to wirelessly communicate with the portable reader.

12. The system of claim 1, wherein each of the plurality of component tags are configured to be attached to the respective component identified thereby and the root tag is configured to be attached on or near the healthcare asset.

13. The system of claim 12, wherein the root tag has a root tag visual identifier thereon and each of the plurality of component tags has a component tag visual identifier thereon.

14. The system of claim 13, wherein the plurality of component tags are configured in a hierarchical structure including parent component tags having at least one child component tag associated therewith and at least one leaf component tag having no child component tag associated therewith, wherein each parent component tag has a parent tag visual identifier thereon and each leaf component tags has a leaf tag visual identifier thereon.

15. A method of identifying a healthcare asset, the method comprising:

providing a set of tags each attached to, integrated into, or near the healthcare asset, the set of tags configured to communicate with one another;

configuring the set of tags to communicate in a hierarchical structure;

operating the tags to communicate an asset identifier identifying the healthcare asset and a plurality of component identifiers identifying components of the healthcare asset, wherein the tags communicate in the hierarchical structure;

receiving the asset identifier and the plurality of component identifiers at a receiver system;

determining a component structure of the healthcare asset based on the hierarchical structure of communications between the tags; and generating, at the receiver system, a bill of materials (BOM) representative of the component structure of the healthcare asset based on the asset identifier and the plurality of component identifiers.

16. The method of claim 15, wherein configuring the set of tags to communicate in the hierarchical structure based on the component structure of the healthcare asset includes:

storing the asset identifier on one of the set of tags so as to configure a root tag associated with the healthcare asset; and storing a different one of the plurality of component identifiers on each remaining tag in the set of tags so as to configure a plurality of component tags.

17. The method of claim 16, wherein configuring the set of tags to communicate in the hierarchical structure based on the component structure of the healthcare asset further includes, for each of the component tags, storing a parent ID thereon and configuring each component tag to transmit its parent ID in conjunction with its component identifier.

18. The method of claim 17, wherein configuring the set of tags to communicate in the hierarchical structure based on the component structure of the healthcare asset further includes, operating each parent component tag to:

identify the one or more component tags that transmit the parent ID corresponding thereto as a child component tag; and receive the component identifier from each child component tag associated therewith.

19. The method of claim 18, further comprising operating each parent component tag to transmit the component identifier received from each child component tag in conjunction with its component identifier and its parent ID, and operating the root tag to transmit the component identifiers from all component tags in the hierarchical structure.

20. The method of claim 18, wherein each parent component tag is configured to detect a missing component identifier for one of its child component tags and to transmit a missing component event in conjunction with its component identifier and its parent ID.

* * * * *